United States Patent
Cogill et al.

(10) Patent No.: US 9,952,190 B2
(45) Date of Patent: Apr. 24, 2018

(54) SYSTEM AND METHOD FOR AIR-POLLUTANT SOURCE-LOCALIZATION USING PARKED MOTOR VEHICLES

(71) Applicant: INTERNATIONAL BUSINESS MACHINES CORPORATION, Armonk, NY (US)

(72) Inventors: Randall L. Cogill, Malahide (IE); Olivier Gallay, Zurich (CH); Chungmok Lee, Castleknock (IE); Zubair Nabi, Ellis Quay (IE); Martin Rufli, Winterthur (CH); Robert Shorten, Mulhuddart (IE); Tigran Tchrakian, Castleknock (IE); Rudi Verago, Ashtown (IE); Fabian R. Wirth, Bremen (DE); Sergiy Zhuk, Clonee (IE)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/746,364

(22) Filed: Jun. 22, 2015

(65) Prior Publication Data
US 2016/0290979 A1    Oct. 6, 2016

Related U.S. Application Data

(63) Continuation of application No. 14/675,154, filed on Mar. 31, 2015.

(51) Int. Cl.
*G01N 33/00* (2006.01)
*G01N 1/22* (2006.01)
(Continued)

(52) U.S. Cl.
CPC ....... *G01N 33/0075* (2013.01); *G01N 1/2273* (2013.01); *G01N 33/0004* (2013.01);
(Continued)

(58) Field of Classification Search
CPC .. B60H 1/00778; B60H 1/008; G01N 1/2273; G01N 2001/021; G01N 15/06;
(Continued)

(56) References Cited

U.S. PATENT DOCUMENTS 5,742,053 A * 4/1998 Rekunyk ................ G01V 9/007
                                                            250/253
6,276,192 B1   8/2001 Sim et al.
(Continued)

FOREIGN PATENT DOCUMENTS

| CN | 103969701 A | 8/2014 |
|----|-------------|--------|
| EP | 0622625 A2 | 11/1994 |
| WO | 2014068376 A1 | 5/2014 |

OTHER PUBLICATIONS

Liu, Jen-Hao, et al. "Developed urban air quality monitoring system based on wireless sensor networks." Sensing Technology (ICST), 2011 Fifth International Conference on. IEEE, 2011.*
(Continued)

*Primary Examiner* — Harshad R Patel
*Assistant Examiner* — Punam Roy
(74) *Attorney, Agent, or Firm* — Tutunjian & Bitetto, P.C.; Kurt Goudy

(57) ABSTRACT

A method for localizing the source of air pollution that includes receiving pollution data from a network in communication with at least one air pollution sensor that is connected to at least one motor vehicle in a stationary position. Each stationary motor vehicle of the network is positioned at a different air pollution measurement location. The method may further include determining from the pollution data an origin of an air pollutant using an air pollution model provided by a pollutant source localization device including at least one hardware processor.

8 Claims, 6 Drawing Sheets

(51) Int. Cl.
G01S 19/14 (2010.01)
G01S 19/42 (2010.01)
G01N 1/02 (2006.01)
B60H 1/00 (2006.01)
G01N 15/00 (2006.01)
G01N 15/06 (2006.01)

(52) U.S. Cl.
CPC ....... *G01N 33/004* (2013.01); *G01N 33/0036* (2013.01); *G01N 33/0037* (2013.01); *G01N 33/0042* (2013.01); *G01N 33/0044* (2013.01); *G01N 33/0062* (2013.01); *G01S 19/14* (2013.01); *G01S 19/42* (2013.01); *B60H 1/00778* (2013.01); *G01N 15/06* (2013.01); *G01N 2001/021* (2013.01); *G01N 2015/0046* (2013.01)

(58) Field of Classification Search
CPC ....... G01N 2015/0046; G01N 33/0004; G01N 33/0036; G01N 33/0037; G01N 33/004; G01N 33/0042; G01N 33/0044; G01N 33/0062; G01N 33/0075; G01S 19/14; G01S 19/42
See application file for complete search history.

(56) References Cited

U.S. PATENT DOCUMENTS

| | | | | |
|---|---|---|---|---|
| 6,895,310 | B1* | 5/2005 | Kolls | G01M 17/007 341/123 |
| 7,001,445 | B2 | 2/2006 | Petersson et al. | |
| 7,857,892 | B2 | 12/2010 | Marra | |
| 8,509,991 | B2 | 8/2013 | Bai | |
| 2008/0287144 | A1* | 11/2008 | Sabata | H04L 67/12 455/456.6 |
| 2013/0047704 | A1 | 2/2013 | Bae et al. | |

OTHER PUBLICATIONS

Choi, Sukwon, et al. "Micro sensor node for air pollutant monitoring: Hardware and software issues." Sensors 9.10 (2009): 7970-7987.*
Egan, Bruce A., and James R. Mahoney. "Numerical modeling of advection and diffusion of urban area source pollutants." Journal of Applied Meteorology 11.2 (1972): 312-322.*
Tirabassi, T. "Analytical air pollution advection and diffusion models." Water, Air, and Soil Pollution 47.1-2 (1989): 19-24.*
Lanser, D., and Jan G. Verwer. "Analysis of operator splitting for advection-diffusion-reaction problems from air pollution modelling." Journal of computational and applied mathematics 111.1 (1999): 201-216.*
Weimer, James, et al. "An approach to leak detection using wireless sensor networks at carbon sequestration sites." International Journal of Greenhouse Gas Control 9 (2012): 243-253.*
Kale, Miss Sindhu S., and Amairullah Khan. "Development on Gas Leak Detection and Location System Based on Wireless Sensor Networks: A Review." International Journal of Engineering Trends and Technology—vol. 12, No. 6 (2014).*
Hiba, Haj Chhade, et al. "Multiple land mines localization using a wireless sensor network." Information Fusion (FUSION), 2014 17th International Conference on. IEEE, 2014.*
Chhadé, Hiba Haj. Data fusion and collaborative state estimation in wireless sensor networks. Diss. Université de Technologie de Compiègne, Jun. 1, 2015.*
Kolb, Charles E., et al. "Mobile laboratory with rapid response instruments for real-time measurements of urban and regional trace gas and particulate distributions and emission source characteristics." Environmental science & technology 38.21 (2004): 5694-5703.*
Weimer, James, Bruno Sinopoli, and Bruce H. Krogh. "Multiple source detection and localization in advection-diffusion processes using wireless sensor networks." Real-Time Systems Symposium, 2009, RTSS 2009. 30th IEEE. IEEE, 2009.*
Ram, S. Sundhar, and Venugopal V. Veeravalli. "Localization and intensity tracking of diffusing point sources using sensor networks." Global Telecommunications Conference, 2007. GLOBECOM'07. IEEE. IEEE, 2007.*
Moreira, D. M., et al. "The GILTT solution of the advection-diffusion equation for an inhomogeneous and nonstationary PBL." Atmospheric Environment 40.17 (2006): 3186-3194.*
Buske, Daniela, et al. "Air pollution steady-state advection-diffusion equation: the general three-dimensional solution." Journal of Environmental Protection 3.09 (2012): 1124.*
Moreira, D.M. et al., "The state-of-art of GILTT method to simulate pollutant dispersion in the atmosphere," Atmospheric Research 92 (2009): 1-17.*
Hanna, Steven R., Gary A. Briggs, and Rayford P. Hosker Jr. Handbook on atmospheric diffusion. No. DOE/TIC-11223. National Oceanic and Atmospheric Administration, Oak Ridge, TN (USA). Atmospheric Turbulence and Diffusion Lab., 1982.*
Esmail, Samia Fathy Hamed. "Assessment of concentration of air pollutants using analytical and numerical solution of the atmospheric diffusion equation." Thesis submitted 2011, Zagazig University.*
Jacobson, Mark Z., et al. "Development and application of a new air pollution modeling system—part I: Gas-phase simulations." Atmospheric Environment30.12 (1996): 1939-1963.*
Henze, D.K., et al., "Inverse modeling and mapping US air quality influences of inorganic PM2.5 precursor emissions using the adjoint of GEOS-Chem," Atmospheric Chemistry and Physics, vol. 9, Aug. 2009. (pp. 5877-5903).
Jackson, R.B. et al., "Natural Gas Pipeline Leaks Across Washington, DC," Environmental Science and Technology, vol. 48, Issue 3., Jan. 2014. (pp. 2051-2058).
Parra-Guevara, D. et al., "On optimal solution of an inverse air pollution problem: Theory and numerical approach," Mathematical and Computer Modelling, vol. 43, Issues 7-8, Apr. 2006. (pp. 766-778).
Ram, S.S. et al., "Localization and Intensity Tracking of Diffusing Point Sources Using Sensor Networks," Global Telecommunications Conference, Nov. 2007, (pp. 3107-3111).
Volgyesi, P. et al., "Air Quality Monitoring with SensorMap," International Conference on Information Processing in Sensor Networks, Apr. 2008. (pp. 529-530).
Vujadinovica, M. et al., "Locating a Source of Air Pollution Using Inverse Modelling and Pre-computed Scenarios," International Congress on Environmental Modelling and Software, 2008. (pp. 129-133).
List of IBM Patents or Patent Applications Treated as Related.

* cited by examiner

SYSTEM AND METHOD FOR AIR-POLLUTANT SOURCE-LOCALIZATION USING PARKED MOTOR VEHICLES

CROSS REFERENCE TO RELATED APPLICATIONS

This application is a Continuation application of co-pending U.S. patent application Ser. No. 14/675,154, filed on Mar. 31, 2015, incorporated herein by reference in its entirety.

BACKGROUND

Technical Field

The present disclosure relates to determining the location of air pollution sources, and more particularly to measuring air pollution sources using sensors fixed to motor vehicles.

Description of the Related Art

Recently, air pollution at the center of a city or on main roads is on the rise due to increases in motor vehicle traffic. Air pollution is a mixture of solid particles and gases in the air. Car emissions, chemicals from factories, dust, and pollen and mold spores may be suspended as particles. Ozone, a gas, is a major part of air pollution in cities. When ozone forms air pollution, it's also called smog. At present, nations and local governments operate air pollution monitoring stations in order to monitor air pollution levels.

SUMMARY

In one embodiment, the present disclosure provides a method of determining sources of air pollution in a given location, such as a city. In one embodiment, a method for measuring the source of air pollution is provided that includes receiving pollution data from a network in communication with at least one air pollution sensor that is connected to at least one motor vehicle in a stationary position. Each stationary motor vehicle in the network is positioned at a different air pollution measurement location. In some embodiments, the methods determine from the pollution data a location of an air pollutant origin using an air pollution model describing at least one of diffusion and advection of gases provided by a pollutant source localization device including at least one hardware processor.

In another aspect of the present disclosure, a system for determining the source of an air pollutant is provided that may include a network for receiving pollution data on at least one air pollutant from a plurality of stationary motor vehicles at different air quality measuring locations. The pollution data is provided by a plurality of sensors integrated into the stationary motor vehicles. The system may further include a pollutant source localization device including at least one hardware processor that is configured to produce an air pollution model describing at least one of diffusion and advection of gases, wherein integrating the pollution data into the air pollution model provides an origin of a pollutant source for the at least one air pollutant.

In yet another aspect of the present disclosure, a computer program product is provided that includes a non-transistory computer readable storage medium having computer readable program code embodied therein for determining a source of air pollution. In some embodiments, the method executed by the computer program product may include receiving pollution data from a network in communication with at least one air pollution sensor that is connected to at least one motor vehicle in a stationary position. Each stationary motor vehicle in the network is positioned at a different air pollution measurement location. In some embodiments, the methods determine from the pollution data a location of an air pollutant origin using an air pollution model describing at least one of diffusion and advection of gases provided by a pollutant source localization device.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
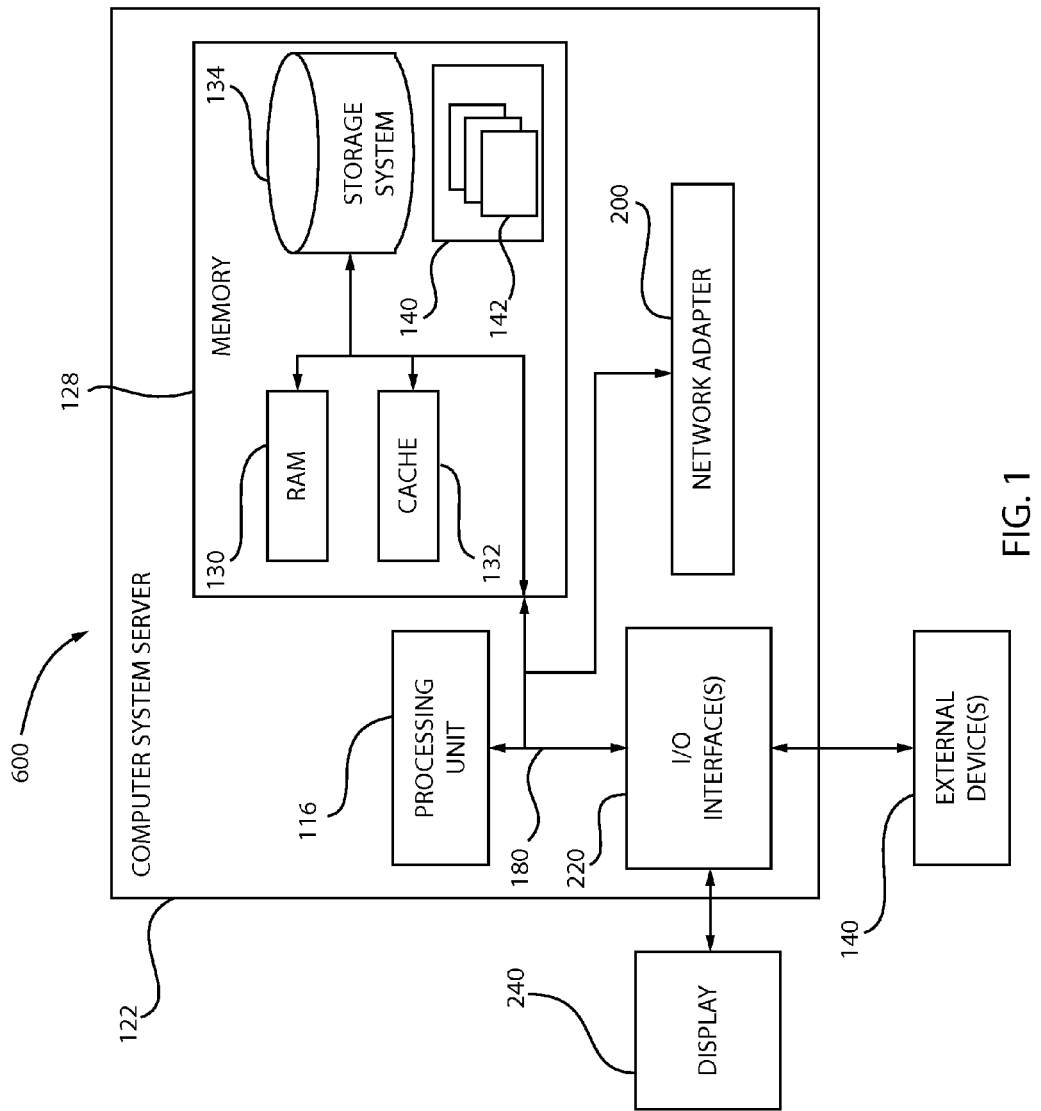
FIG. 1 depicts a cloud computing node according to an embodiment of the present disclosure.

Detailed embodiments of the claimed methods, structures and computer products are disclosed herein; however, it is to be understood that the disclosed embodiments are merely illustrative of the claimed structures and methods that may be embodied in various forms, in addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure. Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

The present disclosure provides for the detection and localization of sources of air pollution using air pollution sensors in motor vehicles. The mechanism for detecting and localizing sources of air pollution in accordance with the present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Therefore, in some embodiments, the computer readable storage medium may be referred to as being "non-transitory".

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be asset bier instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are hound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 600 is only one example of a suitable cloud computing node, and is not ended to suggest any limitation as to the scope of use or functionality of embodiments of the present disclosure described herein. Regardless, cloud computing node 600 is capable of being implemented and/or performing any of the functionality set forth hereinabove.

In cloud computing node 600 there is a computer system/server 122, which is operational with numerous other general purpose or special purpose computing system environments or configurations. Examples of well-known computing systems, environments, and/or configurations that may be suitable for use with computer system/server 122 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 122 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 122 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 122 in cloud computing node 600 is shown in the form of a general-purpose computing device. The components of computer system/server 122 may include, but are not limited to, one or more processors or processing units 116, a system memory 128, and a bus 180 that couples various system components including system memory 128 to processor 116.

Bus 118 represents one or more of any of several types of bus structures, including a memory bus or Memory controller, a peripheral bus, an accelerated graphics port, and a processor or local bus using any of a variety of bus architectures. By way of example, and not limitation, such architectures include Industry Standard. Architecture (ISA) bus, Micro Channel Architecture (MCA) bus, Enhanced ISA (EISA) bus, Video Electronics Standards Association (VESA) local bus, and Peripheral Component interconnects (PCI) bus.

Computer system/server 122 typically includes a variety of computer system readable media. Such media may be any available media that is accessible by computer system/server 122, and it includes both volatile and non-volatile media, removable and non-removable media.

System memory 128 can include computer system readable media in the form of volatile memory, such as random access memory (RAM) 130 and/or cache memory 132. Computer system/server 122 may further include other removable/non-removable, volatile/non-volatile computer system storage media. By way of example only, storage system 134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 118 by one or more data media interfaces. As will be further depicted and described below, memory 128 may include at least one program product having a set (e.g., at least one) of program modules that are configured to carry out the functions of embodiments of the methods, systems and computer program products disclosure herein.

Program/utility 140, having a set (at least one) of program modules 142, may be stored in memory 128 by way of example, and not limitation, as well as an operating system, one or more application programs, other program modules, and program data. Each of the operating system, one or more application programs, other program modules, and program data or some combination thereof, may include an implementation of a networking environment. Program modules 142 generally carry out the functions and/or methodologies of embodiments of the invention as described herein. For example, the program modules 142 may carry out the functions and/or methodologies of the pollution data receiving module 901, and the pollution source localization module 902, which are described below with reference to FIGS. 4-6.

Computer system/server 122 may also communicate with one or more external devices 140 such as a keyboard, a pointing device, a display 240, etc.; one or more devices that enable a user to interact with computer system/server 122; and/or any devices (e.g., network card, modem, etc.) that enable computer system/server 122 to communicate with one or more other computing devices. Such communication can occur via Input/Output (I/O) interfaces 220. Still yet, computer system/server 122 can communicate with one or more networks such as a local area network (LAN), a general wide area network (WAN), and/or a public network (e.g., the Internet) via network adapter 200. As depicted, network adapter 200 communicates with the other components of computer system/server 122 via bus 180. It should be understood that although not shown, other hardware and/or software components could be used in conjunction with computer system/server 122. Examples, include, but are not limited to: microcode, device drivers, redundant processing units, external disk drive arrays, RAID systems, tape drives, and data archival rage systems, etc.

Figure 2:
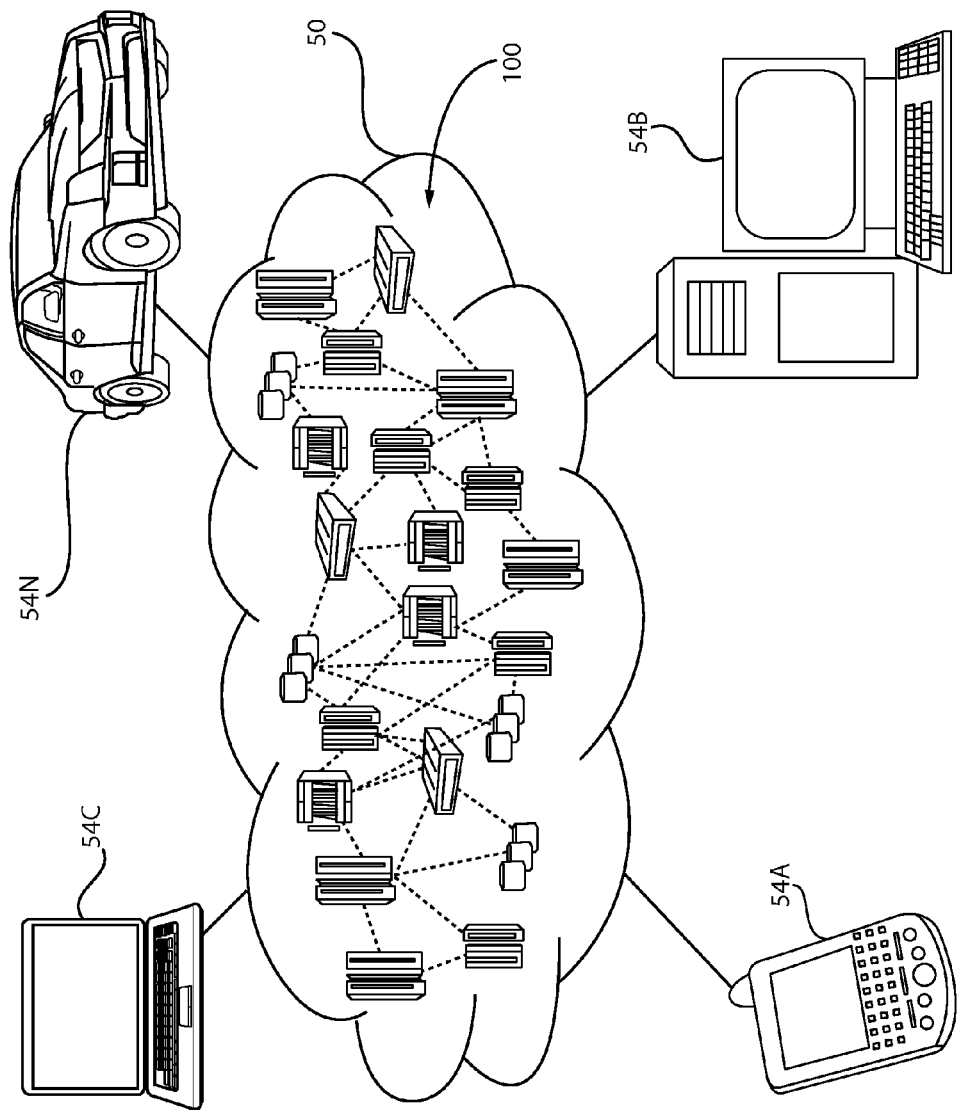
FIG. 2 depicts a cloud computing environment according to an embodiment of the present disclosure.

Referring now to FIG. 2, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. The automobile computer system 54N may include an interface with the air pollution sensors employed to measure the air pollution data for localizing the source of air pollutants in accordance with the methods and systems described with reference to FIGS. 4-6.

Referring to FIG. 2, the nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 100 and cloud computing environment 50 can communicate with any type of computerized device over any type of network and/or network addressable connection (e.g., using a web browser).

Figure 3:
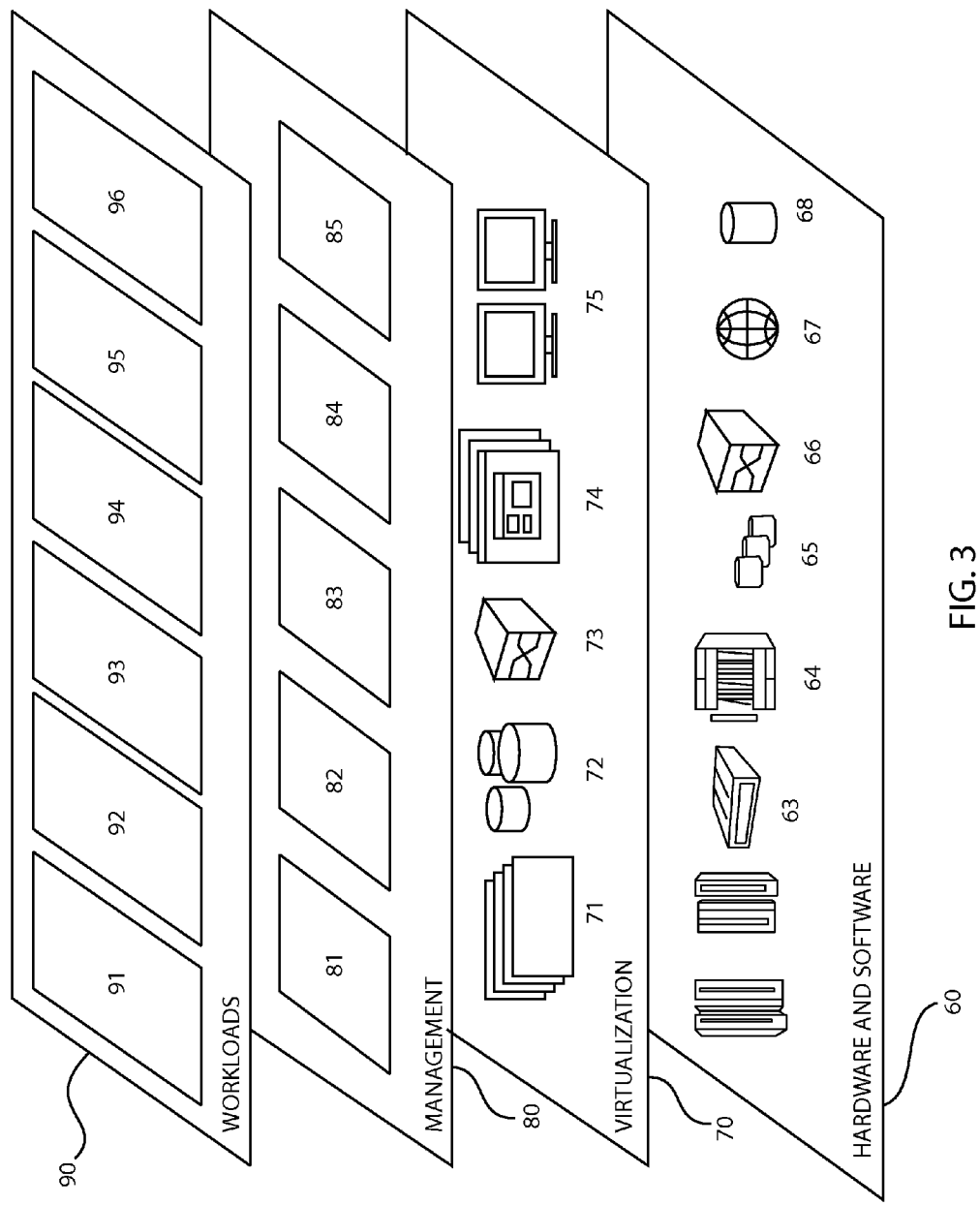
FIG. 3 depicts abstraction model layers according to an embodiment of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the systems, methods and computer program are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and secure communication processing 96. The secure communication processing 96 provided by workload layer 90 may include functions and/or methodologies of the pollution data receiving module 901, and the pollution source localization module 902, which are described below with reference to FIGS. 4-6.

Typically, an air pollutant is a substance in the air that can have adverse effects on humans and the ecosystem. The substance can be solid particles, liquid droplets, or gases. A pollutant can be of natural origin or man-made. Pollutants are classified as primary or secondary. Primary pollutants are usually produced from a process, in which examples include carbon monoxide gas from motor vehicle exhaust, or the sulfur dioxide released from factories. Secondary pollutants are not emitted directly. Rather, they form in the air when primary pollutants react or interact. Ground level ozone is a prominent example of a secondary pollutant. Some pollutants may be both primary and secondary: they are both emitted directly and formed from other primary pollutants.

One example of a primary pollutant produced by human activity is sulfur oxides ($SO_x$). In particular, sulfur dioxide, i.e., a chemical compound with the formula $SO_2$, is produced by various industrial processes. Further, coal and petroleum often contain sulfur compounds, and their combustion generates sulfur dioxide. Additionally, oxidation of $SO_2$, usually in the presence of a catalyst such as $NO_2$, forms $H_2SO_4$. Another example of a primary pollutant is nitrogen oxide, which can have the chemical formula $NO_x$. Nitrogen oxides, particularly nitrogen dioxide ($NO_2$), can expelled from high temperature combustion. Yet, another example of a primary pollutant is carbon monoxide (CO). In some examples, carbon monoxide can be the byproduct of incomplete combustion of fuel, such as natural gas, coal or wood. Vehicular exhaust is a major source of carbon monoxide. Volatile organic compounds (VOCs) are another form of primary pollutant, which can be categorized as either methane ($CH_4$) or non-methane (NMVOCs). Methane is an extremely efficient greenhouse gas that contributes to enhance global warming. Other hydrocarbon VOCs are also significant greenhouse gases, because of their role in creating ozone and prolonging the life of methane in the atmosphere. The aromatic NMVOCs benzene, toluene and xylene are also examples of air pollutants, 1,3-butadiene is another dangerous compound often associated with industrial use. Other examples of primary pollutants include particulate matter (PM), atmospheric particulate matter, or fine particles, which are tiny particles of solid or liquid suspended in a gas. In contrast, aerosol refers to combined particles and gas. Human activities, such as the burning of fossil fuels in vehicles, power plants and various industrial processes also generate significant amounts of aerosols. Other examples of primary pollutants include persistent free radicals; toxic metals, such as mercury and lead; chlorofluorocarbons; ammonia; odors, such as from garbage, sewage, and industrial processes; radioactive pollutants and any combination thereof.

Secondary pollutants may include particulates created from gaseous primary pollutants and compounds in photochemical smog. Smog is a one form of secondary air pollution. Smog can result from large amounts of coal burning in an area caused by a mixture of smoke and sulfur dioxide. Modern smog does not usually come from coal, but from vehicular and industrial emissions that are acted on in the atmosphere by ultraviolet light from the sun to form secondary pollutants that also combine with the primary emissions to form photochemical smog. Secondary pollutants may further include ground level ozone ($O_3$) that can be formed from $NO_x$ and VOCs. Ozone ($O_3$) is a key constituent of the troposphere. Peroxyacetyl nitrate (PAN) is another pollutant that is similarly formed from $NO_x$ and VOCs. Minor air pollutants that can also be detected by the systems, methods and computer products disclosed herein can include any number of minor hazardous air pollutants, such as persistent organic pollutants. Persistent organic pollutants (POPs) are organic compounds that are resistant to environmental degradation through chemical, biological, and photolytic processes.

The sources of the air pollution detected by the methods, systems and computer program products disclosed herein may be anthropogenic (man-made) sources that may be related to the burning of multiple types of fuel. The sources may be stationary sources that include smoke stacks, such as power plants, manufacturing facilities (factories) and waste incinerators, as well as furnaces and other types of fuel-burning heating devices. The sources of air pollution may be mobile sources, such as motor vehicles, marine vessels, and aircraft. In further examples, the sources of the pollutants can result from controlled burn practices in agriculture and forest management. Controlled or prescribed burning is a technique sometimes used in forest management, farming, prairie restoration or greenhouse gas abatement. Other sources of pollutants that can be measured using the methods, systems and computer products of the present disclosure include pollutants from fumes from paint, hair spray, varnish, aerosol sprays and other solvents. Addition sources for air pollution that cat be measured by the methods, systems and computer program products of the present disclosure may include waste deposition in landfills; military resources: such as nuclear weapons, toxic gases, germ warfare and rocketry; and natural sources. Some examples of natural sources for air pollution generation may include dust, methane, radon gas, smoke and carbon monoxide from wildfires, VOC emitting vegetation, and volcanic activity.

In some other embodiments, the air pollutant may be natural gas and/or propane, and the pollutant source may be provided by a natural gas and/or propane leak. Natural gas is a hydrocarbon gas mixture consisting primarily of methane, but commonly includes varying amounts of other higher alkanes and sometimes a usually lesser percentage of carbon dioxide, nitrogen, and/or hydrogen sulfide. Propane is a three-carbon alkane with the molecular formula $C_3H_8$. In these examples, determining the pollutant source, the methods, systems and structures disclosed herein may discover the source of natural gas and propane leaks.

Figure 4:
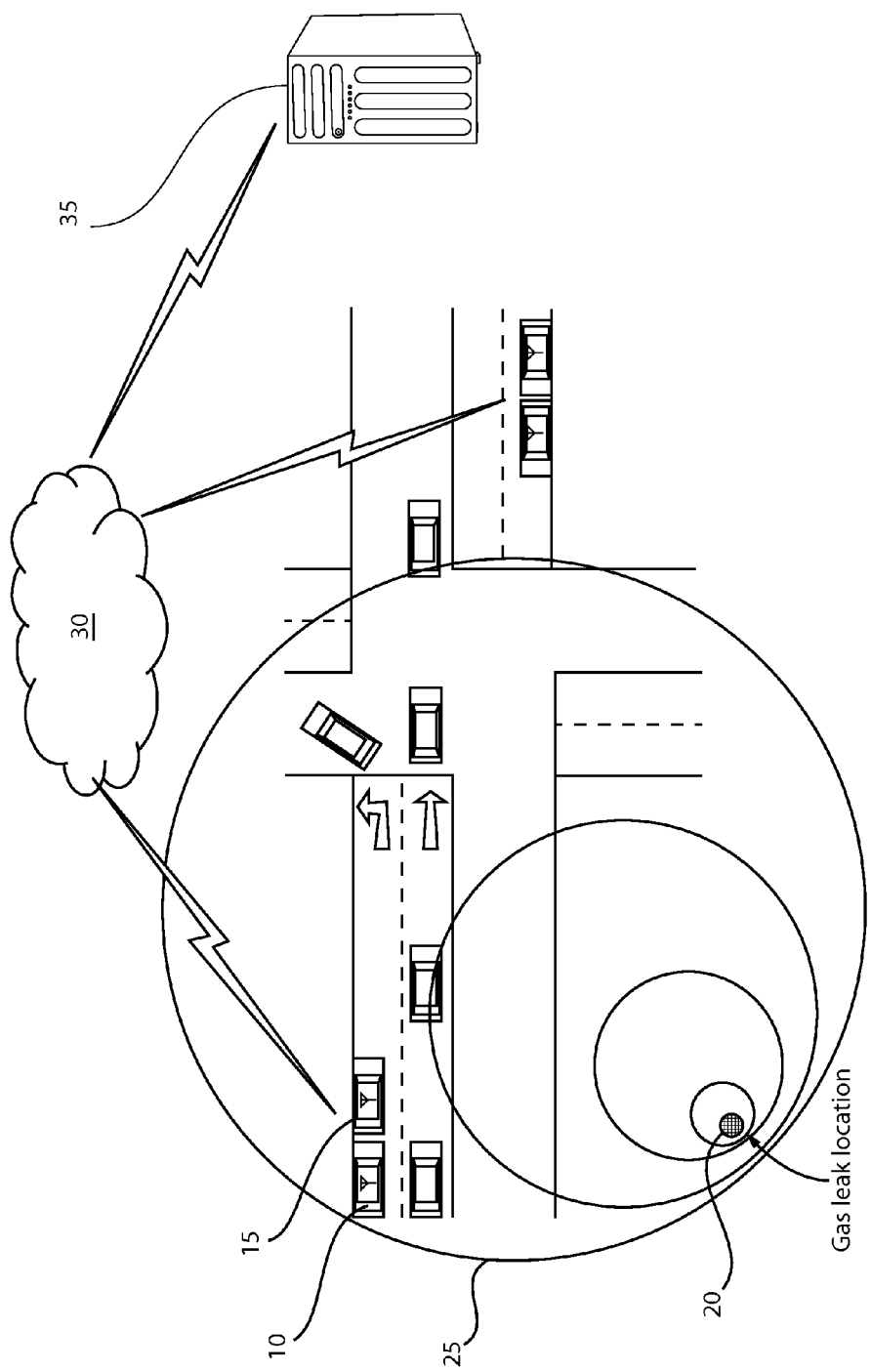
FIG. 4 is a schematic view of a system for determining the source of an air pollutant using at least one stationary motor vehicle, in accordance with one embodiment of the present disclosure.

Referring now to FIG. 4, in some embodiments, the disclosed methods, systems and computer program products detect and localize sources of air pollution using sensors in motor vehicles 10. The term "motor vehicle" as used throughout the specification refers to any moving vehicle that is powered by a form of energy. In some examples, the motor vehicle 10 is capable of carrying one or more human occupants. The term "motor vehicle" includes, but is not limited to: cars, trucks, vans, minivans, sport utility vehicles (SUVs), motor cycles, scooters, boats, personal watercraft and aircraft, such as drones. The form of energy may be provided by an engine. The term "engine" as used throughout the specification refers to any device or machine that is capable of converting energy. In some cases, potential energy is converted to kinetic energy. For example, energy conversion can include a situation where the chemical potential energy of a fuel or fuel cell is converted into rotational kinetic energy or where electrical potential energy is converted into rotational kinetic energy. Engines can also include provisions for converting kinetic energy into potential energy. For example, some engines include regenerative braking systems where kinetic energy from a drivetrain is converted into potential energy. Some examples of engines include, but are not limited to: internal combustion engines, electric motors, solar energy converters, turbines, nuclear power plants, and hybrid systems that combine two or more different types of energy conversion processes.

Figure 5:
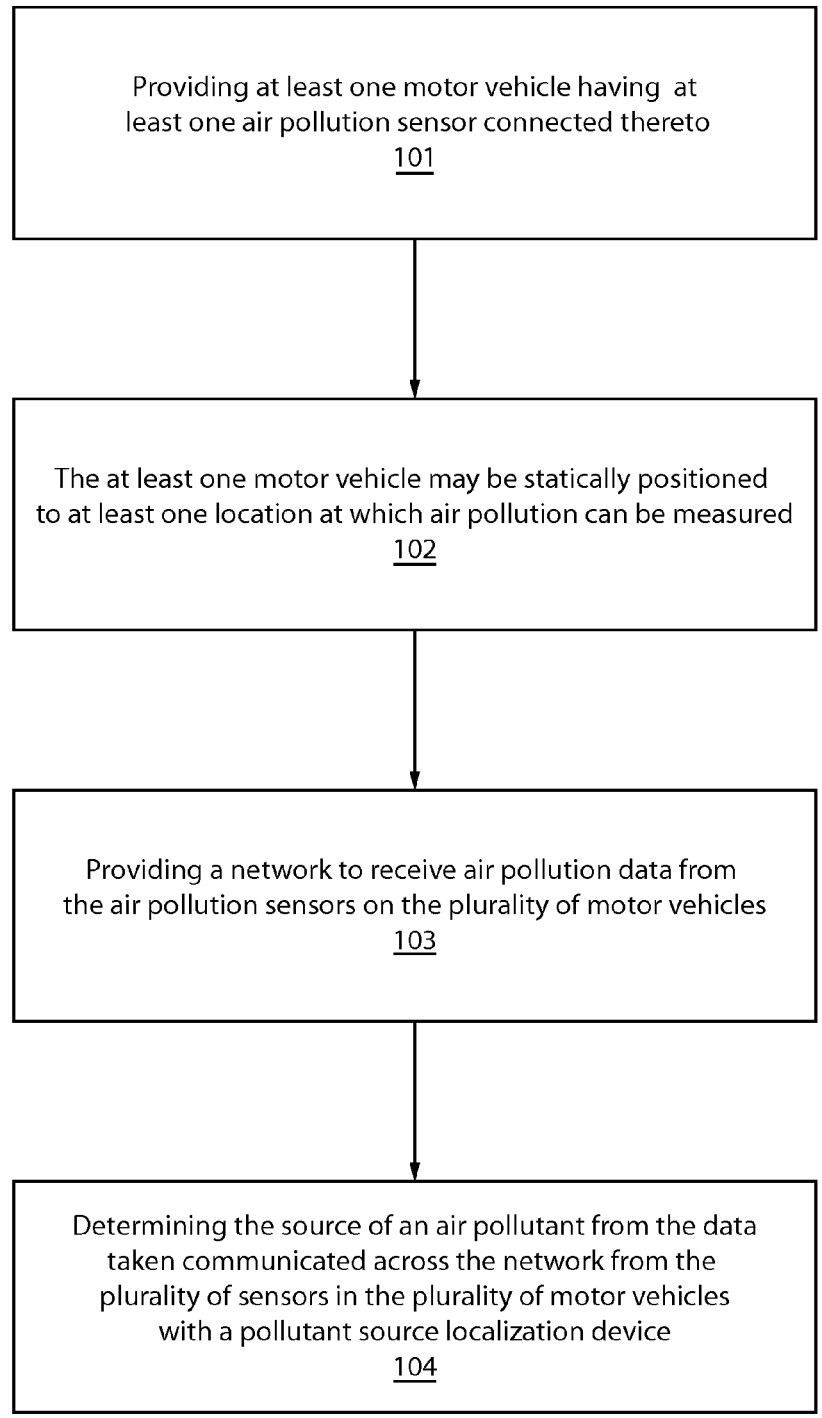
FIG. 5 is a block/flow diagram depicting one embodiment of a method of determining the source of an air pollutant using air pollution sensors mounted to at least one stationary motor vehicle, in accordance with one embodiment of the present disclosure.

In some embodiments, the motor vehicles 10 include umber of air pollution sensors 15 for detecting and localizing sources 20 (also referred to as pollution sources) of air pollution 25. More specifically, as will be described in further detail below, the present disclosure provides a system of air pollution sensors 15 mounted on motor vehicles, which are capable of reporting the pollution data to a central unit, e.g., pollutant source localization device 35. The pollutant source localization device 35 may be interconnected with sensors 15 through a network 30. As illustrated in FIG. 5, in some embodiments of the method of the present disclosure, the method may begin at step 101 with providing at least one motor vehicle 10 having at least one air pollution sensor 15 connected thereto. The air pollution sensors 15 are for measuring pollution data, and can be mounted to the motor vehicles 10 using any means possible, e.g., mechanically, adhesively, or the sensors 115 may be multi-function and provide an additional measurement for the functioning of the motor vehicle 10, or system within the motor vehicle 10, that is not used in the systems, methods, and computer program products disclosed herein. In some embodiments, the air pollution sensors 15 may also provide wind data to be measured at the location where the motor vehicle is measuring the air pollution data. It is not necessary that the air pollution sensors 15 measure wind data, because wind data may be measured from separate sensors integrated into the motor vehicle, as well as be provided by another source, such as a weather model that is run alongside the advection-diffusion partial differential equation (PDE) model described below.

The term "pollution data" denotes a characterization of pollution in air. For example, pollution data may include a measurement of air composition including a pollutant composition and a concentration of pollutant in air. In some embodiments, the system of air pollution sensors 15 may be mounted on motor vehicles 10, in which the air pollution sensors 15 are capable of measuring pollution data, such as pollutant concentration, in the vicinity of the motor vehicle 10, as well as providing data on the location of the motor vehicle 10 reporting the pollution data, and the time at which the pollution data was taken, as depicted in FIG. 4. As depicted in FIG. 4, each of the plurality of motor vehicles 10 may be positioned at different pollution measurement locations throughout a site for measuring pollution data, such as an area surrounding a building, a town, a county, a state, a nation or a combination thereof.

An air pollution sensor 15 that is suitable for use with the present disclosure may include a sensing element, i.e., active element, that is exposed to the air being monitored and sensor circuitry or other components required for operation of the sensor 15. In one embodiment, air pollution sensors 15 that are suitable for being mounted to a motor vehicle 10, and for measuring air pollution data, may include gas sensors. In some examples, the air pollution sensors 15 may include one or more sensors to detect gases, such as ozone ($O_3$), sulfur dioxide ($SO_2$), carbon monoxide, carbon dioxide, lead (Pb), mercury (Hg), Total VOCs (TVOC's), nitric oxide (NO), nitrogen dioxide ($NO_2$), ammonia, air acidity or alkalinity, specific VOC's such as formaldehyde, or any other gases that have been described above for air pollution, i.e., primary and secondary air pollutants. While these particles can range in size, they are typically characterized into one of two groups. A standard for PM10 particles has been established to provide protection for effects associated with thoracic coarse particles having diameters up to 10 micrometers. "Fine particles" are defined as being up to 2.5 micrometers in diameter.

In some embodiments, when the air pollution sensors 15 are being employed to detect the presence of carbon monoxide (CO) including pollutants the sensing element of the sensor 15 may be an electrochemical cell type or a metal oxide semiconductor (MOS) type. In some embodiments, when the sensors 15 are being employed to detect the presence of nitrogen dioxide ($NO_2$), the sensor element of the sensor 15 may be a metal oxide semiconductor (MOS). In some embodiments, when the sensors 15 are being employed to detect the presence of ozone ($O_3$), the sensor element of the sensor 15 may be a UV adsorption active element, metal semiconductor oxide (MOS), electrochemical cell, light scattering (mass concentration type) sensor element, light scattering (laser particle counter) sensor element or a combination thereof.

One example of a sensor 15 including a metal oxide semiconductor sensing element includes a Series 500 air pollution sensor available from Aeroqual ltd. One example of a sensor 15 including an electrochemical cell includes a High-Resolution CO Measurer Model T15v available from Langan, Inc. (using DataBear measuring). One example of a sensor 15 that employs UV adsorption to measure air pollutants is model 202 detector available from 2B Technologies Inc. (FEM EQOA-0410190). One example of a sensor 15 that employs an electromechanical cell as the active sensing element of the sensor 15 can be provided by OMC-1108 ozone monitor. Some examples of sensors 15 that employs an electrochemical cell as the active sensing element of the sensor 15 can be provided by a light scattering/mass concentration active element can be provided by 831 Aerosol Mass Monitor available from Met One Instruments Inc., or Personal DataRAM, Model pDR1500 from Thermo Scientific Inc. One example of a sensor 15 that employs a light scattering/mass concentration active element can be provided by DC1100 Air Quality Monitor available from Dylos Corp. One example of a sensor 15 that employs a light adsorption active element, e.g., for measuring black carbon (soot), can be provided by microAeth® Model AE51 available from AethLabs.

In some examples, in addition to the sensing element, i.e., active element, of the air pollution sensor 15, the sensor 15 may further include a control unit. The control unit stores the air quality parameter data measured by the sensors. The control unit may include a central computer and controller that controls the functions of the air monitoring unit, i.e., sensing element. Those functions may include, but are not limited to, controlling the flow of air through sensor element and acquisition of sensor data, storage of sensor data in some type of nonvolatile memory or storage media, processing sensor data to provide air quality information and communicating with a remotely located control center, such as across a network. A local display may be provided on the sensor 15, or the motor vehicle 10 to which the sensor 15 is mounted. In some embodiment, the control unit of the sensor 15 can perform data logging while keeping track of different locations of an air sampling sequence.

In some embodiments, the air pollution sensors 15 may incorporate a Global Positioning System (GPS) system. The GPS system may be incorporated into the air pollution sensor 15 itself, or the air pollution sensor 115 may utilize the GPS system of the motor vehicle 10 that the sensor 15 is mounted too. This allows the precise location of the sensor 15, and the pollution data monitored by the sensor 15, to be determined.

The sensors 15 may also include a motion controller to ensure that the sensors 15 are turned off, i.e., are not making pollution measurements, and to turn the sensors 15 on when the motor vehicle 10 that the sensor 15 is mounted to is parked, i.e., stationary. This ensures that pollution measurements are not taken when the motor vehicle 10 is travelling.

It is noted that the methods and systems of the present disclosure typically employ both pollution data and wind data to provide the position at which air pollutants are being generated, i.e., originated. The wind data is not necessarily sensed by the motor vehicles 10 that measure the air pollution data. The wind data may be generated by a weather model, which can be run alongside the advection-diffusion partial differential equation (PDE) model described below.

Referring to FIG. 5, in some embodiments, the method of determining a source 20 of air pollution 25 includes statically positioning motor vehicles 10 in areas in which air pollution 25 is to be measured at step 102, as depicted in FIG. 4. The term "statically positioned" means that the motor vehicle is not moving. For example, the motor vehicle 10 may be parked, as opposed to travelling at speed from a first location to a second location. Any number of motor vehicles 10 may be employed in the system pro ride a network of sensors 15 that are positioned for measuring air pollution 25. For example, 10 to 10,000 motor vehicles may be employed in the systems, methods, and computer products of the present disclosure to provide the network of sensors for determining pollution sources. In another example, 100 to 1,000 motor vehicles may be employed in the systems, methods, and computer products of the present disclosure for determining pollution sources. The motor vehicles may be positioned around any potential source 20 of air pollution 25. In some examples, the source 20 of air pollution 25 may be a gas leak from a natural gas line.

Data sent from the sensor 15 may include sensor data, air quality information derived from the sensor data, wind data, location data and/or any other data required for operation of the system. The systems, methods and computer products of the present disclosure may include a network 30 that the air pollution sensors 15 mounted to the motor vehicles 10 may communicate with. The network 30 for providing communication between the motor vehicles 10 including the air pollution sensors 15 and a pollutant source localization device 35 that is configured to calculate from said pollution data an origin of an air pollutant, i.e., pollution source 20 of air pollution 25. For example, the pollution source 20 may be a gas leak from a natural gas line.

Referring to FIG. 5, in some embodiments, the method of determining the location of the source of air pollutants using air pollution sensors 15 applied to stationary motor vehicles 10 may continue with step 103 with providing a network 30 to receive air pollution data from the air pollution sensors 15 on the plurality of motor vehicles 10. Referring to FIG. 4, in some embodiments, the network 30 is a wireless network that employs the internet. For example, the network 30 may employ a local wireless connection involving a 900 MHz spread spectrum or other transmission technique commonly used in cordless phones. This technique utilizes abase unit transceiver that connects to a local phone line and another transceiver in the motor vehicle 10 and/or air pollution sensors 15. When the sensors 15 need to send or receive data, the unit checks the phone line to determine if it is busy, and if not the unit makes a call and sends or receives data through a local Internet Service Provider (ISP). Another method is to use a cellular phone to directly access a local or remote ISP. Finally, the air monitoring unit may connect to a building control system, e.g., via a WiFi connection, which is connected to the Internet to provide data to the building control system for use by this system and to connect to the Internet. It will be understood that any method of connection to the Internet may be used.

The Internet may be used to transmit information between the sensors 15 that are mounted to the motor vehicles 10 and the pollutant source localization device 35 to initialize or modify its program, operation, and/or setup based on specific information obtained about the sensors 15 that are mounted on the motor vehicles 10 their surrounding environment and known or suspected air pollution. In some embodiments, The sensors 15 measure the concentration of air pollutants 25, tag the pollution data with relevant information, such as time, speed and GPS location, and send the data over a cellular data link to a pollutant source localization device 35, which can be a module on a cloud server, via the network 30, or a server at an operator of the system for determining air pollution sources.

Referring to FIG. 5, in some embodiments, the methods of determining the location of the source of air pollutants using sensors 15 applied to stationary motor vehicles 10 may continue at step 104 by determining the source 20 of an air pollutant from the data taken by the plurality of sensors 14 and communicated across the network 30 with a pollutant source localization device 35. Raw pollution data may be processed and aggregated by a pollution data receiving module of the pollutant source localization device 35. For example, the pollutant source localization device 35 may receive all the data from all the air pollution sensors 15 of the motor vehicles 10 communication with the network 30 to provide a pollution map. The pollution map is one example of a method that may be used to localize a pollution source 20. The pollutant source localization device 35 also employs wind data for determining the source of air pollutants.

In another example, pollution source determining algorithms may be employed to calculate from the pollution data the pollution source 20 using a pollutant source localization module of the pollutant source localization device 35. The pollution source determining algorithms may take into account the position of the motor vehicles 10 including the sensors 15 that are measuring the pollution data, as well as the time that the pollution data is taken, and other environmental factors, such as wind speed and temperature. The wind field ascertained by the wind data need not be very accurate, only the prevailing wind is assumed to be known from the data. The component of the wind that is unknown is accounted for in the algorithm, i.e., advection-diffusion partial differential equation (PDE) model described below.

This parameter is changed depending on how accurately the wind field can be known from the data.

The pollution source determining algorithm may be performed by a tangible device that can retain and store instructions for use by an instruction execution device that includes a hardware processor, such as the processor of a general purpose computer, or a specially designed computer having modules designed to calculate pollutant source data from a plurality of air pollutant sensors 15 mounted to stationary motor vehicles 10 that are positioned at different locations relative to at least one pollution source across a network 30, or other programmable data processing apparatus. In other embodiments, the pollution source determining algorithm may be executed in the cloud computing environment, which can comprise at least one or more cloud computing nodes with which local computing devices, such as, for example, personal digital assistant (PDA) or cellular telephone, desktop computer, laptop computer, and/or automobile computer system may communicate. The nodes may communicate with one another. They may be grouped (not shown) physically or virtually, in one or more networks, such as private, community, public, or hybrid clouds.

In one example, the pollution source determining algorithm may employ an inversion model. The inversion model can be based on Pontryagin maximum principle. In this example, the inversion model takes the entire set of observations, and optimally constructs an initial condition for the chemistry transport model, which matches the observed data in a least-squares sense.

In one example, the pollution source determining algorithm may include a partial differential equation (PDE) model that describes the diffusion and advection of gas. Here, PDE modeling refers to the mathematical description of contaminant transport in the atmosphere. The term dispersion in this context is used to describe the combination of diffusion (due to turbulent eddy motion) and advection (due to the wind) that occurs within the air near the Earth's surface. The concentration of a contaminant released into the air may therefore described by the advection-diffusion equation which is a second-order partial differential equation of parabolic type. In some embodiments, the pollution source determining algorithm may be a gas localization method that can employ a PDE model describing the diffusion and advection of gases carrying pollutants. One example of an advection-diffusion PDE model is as follows:

$$\frac{\partial C}{\partial t} + u\frac{\partial C}{\partial x} + v\frac{\partial C}{\partial y} + w\frac{\partial C}{\partial z} = K_x\frac{\partial^2 C}{\partial x^2} + K_y\frac{\partial^2 C}{\partial y^2} + K_z\frac{\partial^2 C}{\partial z^2}$$

In which C is a scalar concentration field; x, y, z, are space dimensions, t is a time dimension, u, v and w are the velocities in x-, y- and z-directions (wind speed) respectively, and Kx, Ky, Kz are diffusion coefficients. The pollution source determining algorithm, i.e., the advection-diffusion PDE model, provides an estimate of: 1) the localization of air pollution sources; 2) the time at which the emission of pollution at the source began; and 3) the intensity of the air pollution source (wherein the intensity is some measure of concentration).

In this example, each motor vehicle 10 is located at a point in (x, y, z) at time t carries a pollution sensor 15 that communicates values C(x, y, z, t) to the central system, i.e., pollutant source localization device 35. In some embodiments, these sparse measurements of concentration can be used together with the PDE model and wind data to estimate the location, start-time and intensity of a pollutant source 20. The pollutant source 20 may be stationary sources that include smoke stacks, such as power plants, manufacturing facilities (factories) and waste incinerators, as well as furnaces and other types of fuel-burning heating devices. For example, the pollution source 20 may be a gas leak of a natural gas line. The pollutant source 20 of air pollution may be mobile sources, such as motor vehicles, marine vessels, and aircraft. In further examples, the sources of the pollutants can result from controlled burn practices in agriculture and forest management. It is noted that these are only some examples of pollutant sources that can be measured using the above Gaussian model. Any source of pollution can be detected, as long as they are detectable by the air pollution sensors 15. The estimation of the pollutant source may be done by means of model reduction and optimization. Specifically, model reduction techniques are used to solve the PDE, and optimization techniques are used to determine the pollution source parameters.

In some embodiments, the methods, systems, and computer program products disclosed herein can detect the presence of gas leaks, e.g., natural gas leaks and propane gas leaks. In other embodiments, the methods, systems, and computer program products disclosed herein can be used to calibrate fixed sensors that are employed to measure air pollution.

Figure 6:
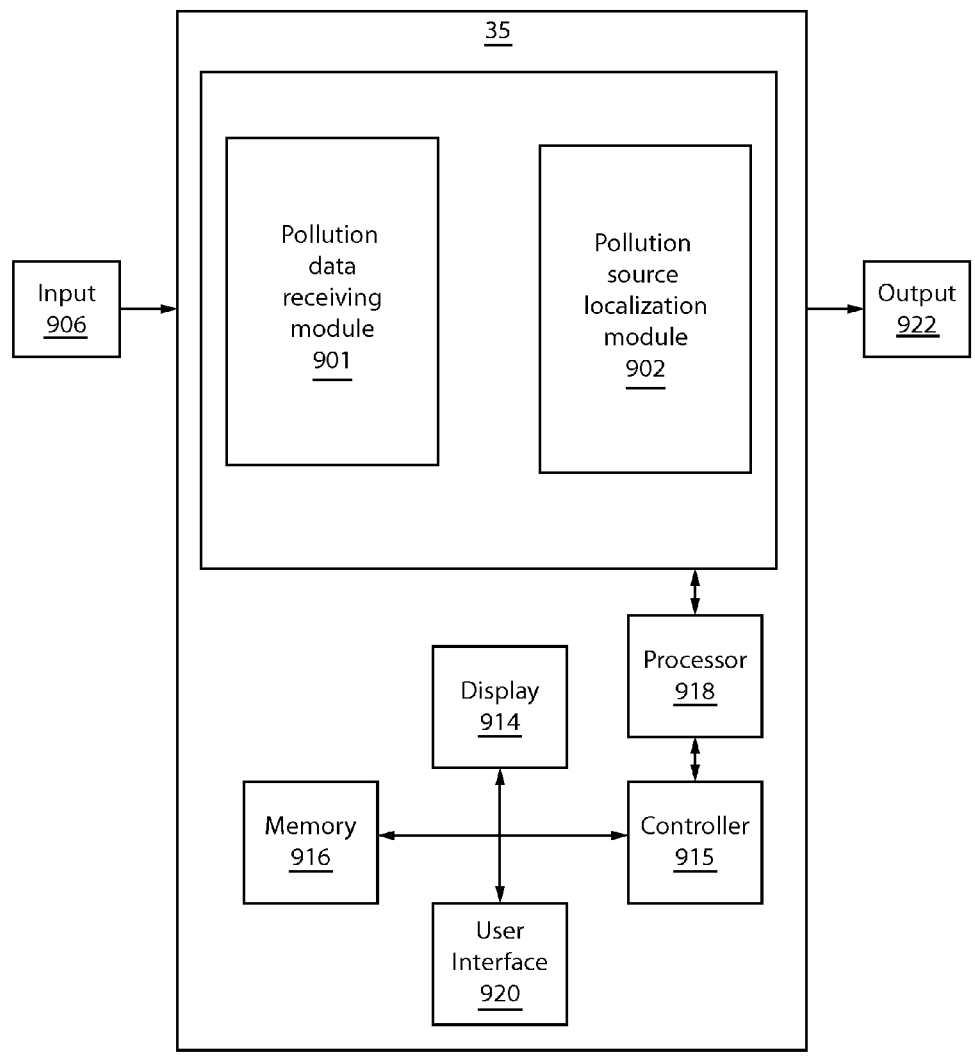
FIG. 6 is a block diagram of a system for determining the source of an air pollutant, in accordance with one embodiment of the present disclosure.

FIG. 6. depicts one embodiment of another aspect of the present disclosure. FIG. 6 depicts one embodiment of a system 900 for determining the source of an air pollutant that includes a network 30 for receiving pollution data from a plurality of stationary motor vehicles 10 at different air quality measuring locations, wherein the pollution data is provided by a plurality of sensors 15 integrated into the stationary motor vehicles 10. The motor vehicles 10 and air pollutant sensors 15, as well as the network 30, have been described above with reference to FIGS. 4 and 5. The system may further include pollutant source localization device 35 that is configured to calculate from the pollution data an origin, i.e., pollution source, of an air pollutant.

In one embodiment, the pollutant source localization device 35 includes one or more processors 918 and memory 916 for storing applications, modules and other data. In one example, the one or more processors 918 and memory 916 may be components of a computer, in which the memory may be random access memory (RAM), a program memory (preferably a writable read-only memory (ROM) such as a flash ROM) or a combination thereof. The computer may also include an input/output (I/O) controller coupled by a CPU bus. The computer may optionally include a hard drive controller, which is coupled to a hard disk and CPU bus. Hard disk may be used for storing application programs, such as some embodiments of the present disclosure, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link.

The system 900 may include one or more displays 914 for viewing. The displays 914 may permit a user to interact with the system 900 and its components and functions. This may be further facilitated by a user interface 920, which may include a mouse, joystick, or any other peripheral or control to permit user interaction with the system 900 and/or its devices, and may be further facilitated by a controller 912. It should be understood that the components and functions of the system 900 may be integrated into one or more systems or workstations. The display 914, a keyboard and a pointing device (mouse) may also be connected to I/O bus of the computer. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

The system 900 may receive input data 902. The input data 902 may be the pollution data measured by the plurality of air pollution sensors 15 integrated with the motor vehicles 10 that is in communication with the pollutant source localization device 35 across the network 30, as depicted in FIG. 4. Referring back to FIG. 6, the pollution data may be employed as input 906 to a plurality of modules 901, 902 of the pollutant source localization device 35, which may include a pollution data receiving module 901 and a pollutant source localization module 902. The system 900 may produce output data 922, which can be the source of a pollutant measured from the sensors as calculated in the pollutant source localization module 902. In one embodiment, data related to the source of the pollutant calculated by the pollutant source localization module 902 may be displayed on one or more display devices 914. It should be noted that while the above configuration is illustratively depicted, it is contemplated that other sorts of configurations may also be employed according to the present principles.

In one embodiment, the pollution data receiving module 901 is configured to receive and store all the pollutant data from the plurality of air pollution sensors of the plurality of motor vehicles. The pollution data receiving module 901 may sort and store data related to pollution composition, pollution concentration, location of sensor measuring the pollution composition and time at which the sensor measured the pollution data. The pollution data receiving module 901 may also sort and store data on the ambient, in which the air pollution measurements were made, which can include temperature, humidity and wind speed. The data sorted and stored by the pollution data receiving module is transmitted to the pollutant source localization module 902 for calculation of a pollutant source.

In one embodiment, the pollutant source localization module 902 is configured to calculate the source of pollutants measured from the network of sensors that are connected to motor vehicles. In some examples, the pollutant source localization module 902 can determine the source of a pollutant using the data sorted by the pollution data receiving module 901 into an air pollution model, such as a Gaussian model describing the diffusion and advection of gases carrying pollutants. For example, using the air pollution model, an estimate concentration of a pollutant over a full domain, or estimate of the location of the pollution source can be calculated. In some embodiments, the estimation may be provided by a model reduction and robust nonlinear control methods for partial differential equations. Further details on the use of the air pollution model, e.g., Gaussian model, as employed by the pollutant source localization module 902 to calculate the location of pollution sources has been described above in the description of step 104 of the process flow for the method illustrated in FIG. 5.

In some embodiments, the methods, systems and computer program products disclosed herein provide a sensor network, i.e., a network of air pollution sensor mounted to motor vehicles that is more pervasive than prior fixed air-quality sensor networks. For example, by using the methods, systems and computer program products disclosed herein, the requirement to deploy fixed sensors across a city that air pollutants are to be measured from can be eliminated, because air pollution sensors can be mounted to motor vehicles that can be switched on, once the motor vehicle is stationary, i.e., parked. Typically, parked cars provide a more precise GPS location for air pollution measurements, when compared with the air pollution measurements taken from moving cars. Further, the pollution measurements provided by the methods, systems and computer program products disclosed herein are more robust when compared to prior air pollution measurement systems. The robustness is at least partially due to the potentially large number of air pollution sensor equipped motor vehicles that may be integrated into the network, which can provide data redundancy. In some embodiments, the systems, methods, and computer program products that are disclosed herein may be integrated with existing the existing fixed air quality sensor infrastructure that is employed by a location.

Having described preferred embodiments of a system and method and computer program product for determining the source of air pollutants using sensors mounted to motor vehicles, it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for measuring air pollution comprising:
receiving pollution data from a network in communication with at least one air pollution sensor that is connected to at least one motor vehicle only in a stationary position; each stationary motor vehicle in said network positioned at a different air pollution measurement location;
measuring a location of the at least one vehicle using a vehicle GPS system, wherein a motion controller that controls said at least one air pollution sensor to stop taking readings when a motion sensor in said at least one air pollution sensor reads that said at least one motor vehicle that is in the stationary position plotted by the vehicle GPS system starts to move; and
determining from said pollution data an origin of an air pollutant using an air pollution model describing at least one of diffusion of gasses and advection of gasses provided by a pollutant source localization device including at least one hardware processor.

2. The method of claim 1, wherein the air pollutant is selected from the group consisting of natural gas, sulfur oxide ($SO_x$), sulfur dioxide ($SO_2$), nitrogen oxide ($NO_x$), nitrogen dioxide ($NO_2$), sulfuric acid ($H_2SO_4$), carbon monoxide (CO), carbon dioxide ($CO_2$), volatile organic compounds (VOCs), methane ($CH_4$), non-methane volatile organic compounds (NMVOCs), particulate matter (PM), atmospheric particulate matter, fine particles, persistent free radicals, toxic metals, mercury, lead, chlorofluorocarbons, ammonia, propane, smog (black carbon) and combinations thereof.

3. The method of claim 1, wherein the pollution data includes at least one of pollutant composition, pollutant concentration, time of pollutant measurement by said at least one air pollution sensor, location of said at least one air pollution sensor during a measurement to provide the pollution data, and wind speed.

4. The method of claim 1, wherein the at least one air pollution sensor comprises an active element selected from the group consisting of an electrochemical cell, a metal oxide semiconductor, UV adsorption active element, light scattering sensor element, and combinations thereof.

5. The method of claim 1, wherein the at least one motor vehicle is selected from the group consisting of cars, trucks, motorcycles, boats, aircraft and a combination thereof.

6. The method of claim 1, wherein the determining of the origin of the air pollutant from said pollution data by the pollutant source localization device includes a partial differential equation (PDE) model describing said at least one of diffusion of said gasses and advection of said gasses carrying pollutants.

7. The method of claim 6, wherein the PDE model comprises:

$$\partial C/\partial t + u\partial C/\partial x + v\partial C/\partial y + w\partial C/\partial z = K_x(\partial^2 C)/\partial x^2 + K_y(\partial^2 C)/\partial y^2 + K_Z(\partial^2 C)/\partial z^2$$

wherein C is a scalar concentration field, x, y, z are space dimensions, t is a time dimension, u, v and w are wind speed velocities in x-, y- and z-directions, and Kx, Ky, Kz are diffusion coefficients.

8. The method of claim 7, wherein the pollutant source being localized is a natural gas leak from a gas pipe.

* * * * *

UNITED STATES PATENT AND TRADEMARK OFFICE
CERTIFICATE OF CORRECTION

| | |
|---|---|
| PATENT NO. | : 9,952,190 B2 |
| APPLICATION NO. | : 14/746364 |
| DATED | : April 24, 2018 |
| INVENTOR(S) | : Randall L. Cogill et al. |

It is certified that error appears in the above-identified patent and that said Letters Patent is hereby corrected as shown below:

On the Title Page

Item (72) Inventors: DELETE "Tigran Tchrakian" and INSERT --Tigran Tigran Tchrakian--

Signed and Sealed this
Fifth Day of December, 2023

Katherine Kelly Vidal
*Director of the United States Patent and Trademark Office*